United States Patent [19]

Wandell

[11] Patent Number: Plant 6,511

[45] Date of Patent: Jan. 3, 1989

[54] STERLING SILVER LINDEN

[76] Inventor: Willet N. Wandell, Rte. #1, Box 286, Oquawka, Ill. 61469

[21] Appl. No.: 945,941

[22] Filed: Dec. 24, 1986

[51] Int. Cl.[4] ..... A01H 5/00

[52] U.S. Cl. ..... Plt./51

[58] Field of Search ..... Plt./51

*Primary Examiner*—Robert E. Bagwill

[57] ABSTRACT

A silver linden tree having a compact form, relatively smooth bark, few flowers and fruits, and healthy foliage.

1 Drawing Sheet

BACKGROUND OF INVENTION

This new selection of silver linden had its origin in a group of seedlings purchased from an unknown source in 1957. I selected from those outplanted in a nursery row at Myra Station Road, Urbana, Ill., six superior plants which have been again transplanted and cultured since that date. This tree, 'Sterling', is the outstanding tree of those selected.

BRIEF DESCRIPTION OF ILLUSTRATIONS

DESCRIPTION OF THE NEW PLANT

Figure 1:
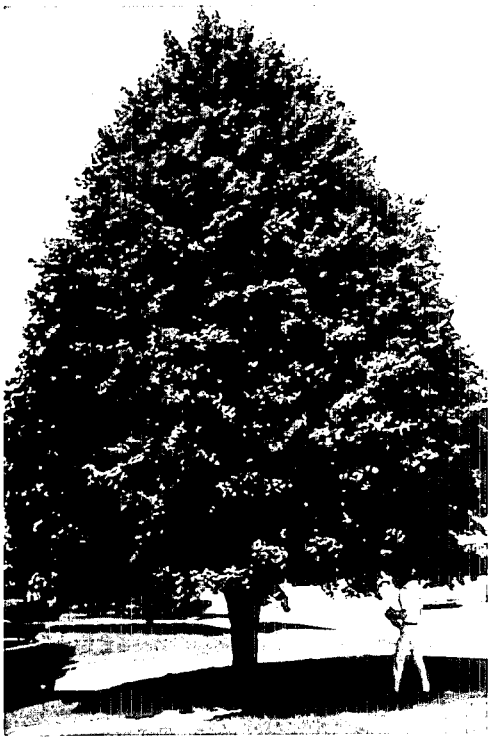
FIG. 1 is a photographic view of my new variety as outplanted.
Figure 2:
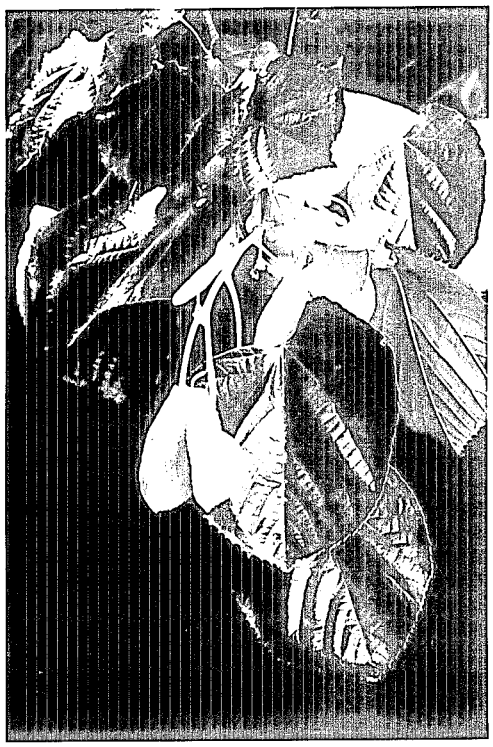
FIG. 2 is a photographic view of the leaves of my new variety as it appears in June.
Figure 3:
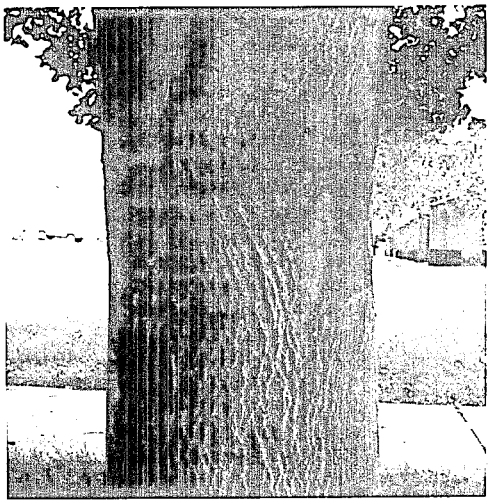
FIG. 3 is a photographic view of the bark of my new variety as it appears in September.
Figure 4:
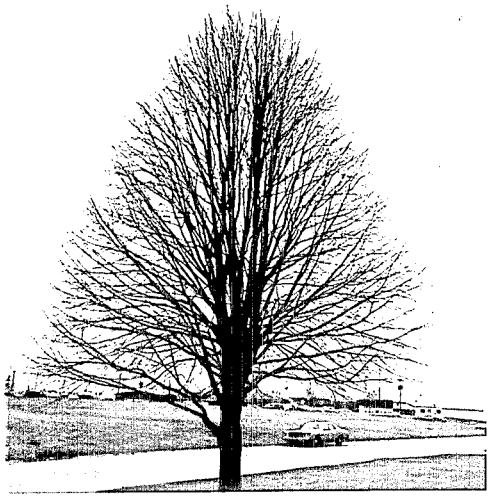
FIG. 4 is a photographic view of my new variety as it appears in December.

The following is a description of my new variety and the stated observations having been made at Urbana, Ill., by applicant.

Origin: Seedling.

Parentage: A tree propagated from seedlings purchased from an unknown source. (Records lost in an office fire of December, 1979.)

Propagation: Maintains its distinguishing characteristics when propagated by budding.

Classification: *Tilia tomentosa* var. 'Sterling'.

Form: A moderately-pyramidal shaped tree with a heavy leaf population configured in a tight-shaped symmetrical crown.

Habit: Upright tree forming a multiple leader well above the ground, with tightly ascending branch scaffold. Crown moderately-pyramidal in shape, dense, tight, neatly symmetrical measuring 45 feet tall and 24 feet broad in a 29 year old tree. Branches moderately-fine, first year shoots completely covered with silvery stellate hairs, the older shoot pubescent and light brown, becoming orange-brown, green and finally gray-brown. Leaf scars alternate, 2 ranked, half elliptical, slightly raised, with 3 bundle-traces.

Winter buds: Solitary, ovoid, reddish brown, with 4 exposed bud scales, the exposed parts covered with stellate trichomes; terminal bud present.

Bark: Light gray and smooth on branch up to 8" in diameter, large branches and trunk gray-brown with shallow furrows and smooth, flat ridges.

Leaves: Alternate, simple, deciduous, petiolate; blades subcircular in outline, the base strongly asymmetrical with one pronounced rounded lobe, the apices shortly acuminate, the margins sharply serrate, the upper surface dark green and corresponding with *The Royal Horticultural Society Color Chart* #136 A, lustrous, and glabrous at maturity, the lower surface tomentose with silvery stellate trichomes, varying in size on a tree mostly from 2½ to 4" long and 2 to 3½" wide, young leaves silvery-tomentose above and below; petioles 1½ to 2' long, silvery tomentose; fall color rusty yellow.

Flowers: Produced sparsely rather late, the first of July in Urbana, Ill.; in 3–7 flowered pendulous cymes on the silvery-tomentose bracts; sepals 5, symbiform, silvery-tomentose exceeding the petals in length, in fascicles, staminodes absent; gynoecium of one compound pistil, the ovary silvery-tomentose; apparently have a narcotic effect on honey bees and possibly some other insects resulting in possible lack of fertilization and many aborted embryos.

Fruit: Nut-like, silvery-tomentose, becoming brown, globose, faintly 5-angled, 8–10 mm in diameter, few in quantity and mostly persistant on tree.

I claim:

1. A new and distinctive variety of *Tilia tomentosa,* named 'Sterling' is described herein that differs from other varieties by the unique combination of: (1) moderately-pyramidal, very symmetrical, tight, dense crown instead of the variable, pendulous, hemispherical or broadly-domed crown of the species; (2) the consistently tight ascending multiple branching in the upper one-half of the trunk; (3) the leaves that are completely silvery-tomentose when young, becoming dark green and lustrous above at maturity; (4) the smooth beech-like bark; (5) the sparse production of flowers and fruit; and (6) the overall neatness of the tree with healthy foliage throughout the growing season and general lack of messy fruit.

* * * * *